(12) United States Patent
Eom et al.

(10) Patent No.: US 10,913,700 B2
(45) Date of Patent: Feb. 9, 2021

(54) METHOD FOR PRODUCING DIMETHYLOLBUTANAL AND DISTILLATION APPARATUS FOR PRODUCING SAME

(71) Applicant: LG CHEM, LTD., Seoul (KR)

(72) Inventors: Sungshik Eom, Daejeon (KR); Dawon Jung, Daejeon (KR); Tae Youn Kim, Daejeon (KR); Dong Hyun Ko, Daejeon (KR); Mi Young Kim, Daejeon (KR); Min Ji Choi, Daejeon (KR); Taewoo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/769,187

(22) PCT Filed: Jan. 24, 2019

(86) PCT No.: PCT/KR2019/001012
§ 371 (c)(1),
(2) Date: Jun. 2, 2020

(87) PCT Pub. No.: WO2019/151710
PCT Pub. Date: Aug. 8, 2019

(65) Prior Publication Data
US 2020/0369588 A1    Nov. 26, 2020

(30) Foreign Application Priority Data
Feb. 1, 2018 (KR) .................. 10-2018-0013043

(51) Int. Cl.
C07C 45/83 (2006.01)
B01D 3/00 (2006.01)
B01D 3/32 (2006.01)
B01D 3/14 (2006.01)

(52) U.S. Cl.
CPC .............. *C07C 45/83* (2013.01); *B01D 3/009* (2013.01); *B01D 3/143* (2013.01); *B01D 3/32* (2013.01)

(58) Field of Classification Search
CPC ......... C07C 45/72; C07C 45/73; C07C 45/83; B01D 3/006; B01D 3/143; B01D 3/32
See application file for complete search history.

(56) References Cited

U.S. PATENT DOCUMENTS

| | | |
|---|---|---|
| 7,253,326 B1 | 8/2007 | Eom et al. |
| 2002/0189926 A1 | 12/2002 | Dernbach et al. |
| 2003/0088131 A1 | 5/2003 | Dernbach et al. |
| 2003/0139631 A1 | 7/2003 | Muller et al. |
| 2004/0267055 A1 | 12/2004 | Sirch et al. |
| 2007/0112221 A1 | 5/2007 | Konishi et al. |
| 2011/0313203 A1 | 12/2011 | Sirch et al. |
| 2017/0333808 A1 | 11/2017 | Lee et al. |

FOREIGN PATENT DOCUMENTS

| | | |
|---|---|---|
| JP | 2017-534603 A | 11/2017 |
| KR | 2002-0062380 A | 7/2002 |
| KR | 2002-0062666 A | 7/2002 |
| KR | 2003-0057363 A | 7/2003 |
| KR | 2005-0044718 A | 5/2005 |
| KR | 10-0837523 B1 | 12/2008 |
| KR | 2011-0098941 A | 9/2011 |
| KR | 10-1804006 B1 | 12/2017 |
| WO | 2005/007605 A1 | 1/2005 |

*Primary Examiner* — Sikarl A Witherspoon
(74) *Attorney, Agent, or Firm* — Dentons US LLP

(57) ABSTRACT

A method for producing dimethylolbutanal, the method including: (A) distilling a raw material comprising dimethylolbutanal (DMB) in a distillation column; (B) separating the distilled raw material in the distillation column into a low boiling point component, dimethylolbutanal, and a high boiling point component; and (C) refluxing a portion or all of the high boiling point component to the distillation column by heating the portion or all of the high boiling point component, in which the dimethylolbutanal is separated from a side cut of the distillation column.

17 Claims, 2 Drawing Sheets

[Figure 1]
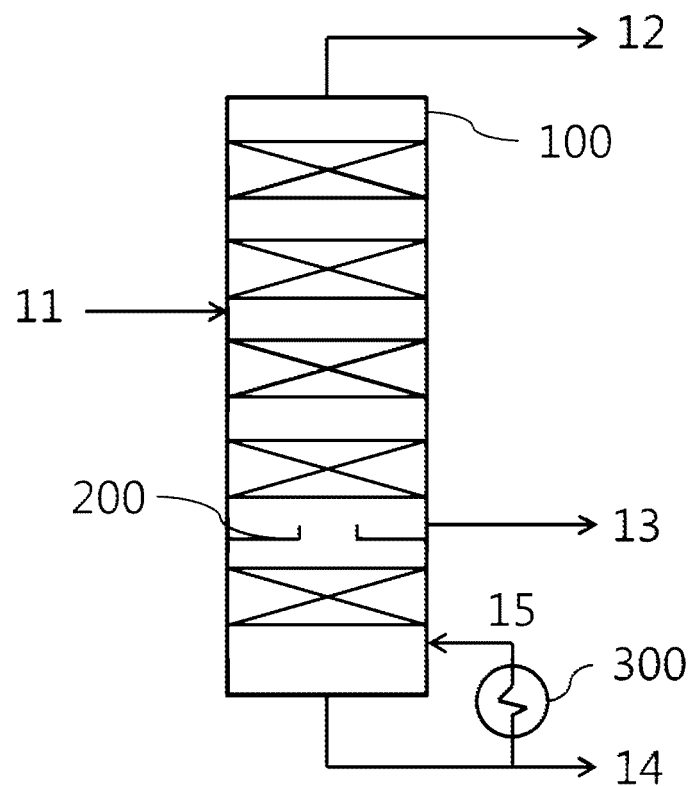

[Figure 2 - RELATED ART]
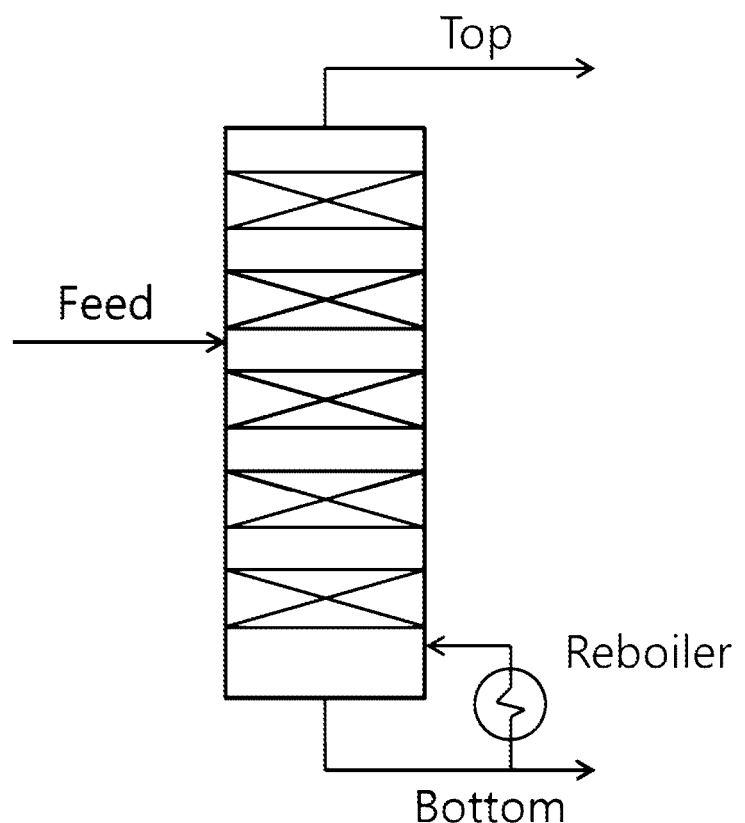

METHOD FOR PRODUCING DIMETHYLOLBUTANAL AND DISTILLATION APPARATUS FOR PRODUCING SAME

CROSS-REFERENCE TO RELATED APPLICATIONS

This application is a U.S. national stage of international Application No. PCT/KR2019/001012 filed Jan. 24, 2019, and claims priority to and the benefit of Korean Patent Application No. 10-2018-0013043 filed in the Korean Intellectual Property Office on Feb. 1, 2018, the entire contents of which are incorporated herein by reference.

TECHNICAL FIELD

The present specification relates to a method for producing dimethylolbutanal and a distillation device for producing same.

BACKGROUND

Trimethylolpropane (TMP) is a white crystalline substance at room temperature, and is widely used as a raw material in various fields such as alkyd resins, saturated polyesters, synthetic lubricants, polyurethane resins, and plasticizers-.

Trimethylolpropane as an industrially important raw material may be produced by various methods, including a method for producing trimethylolpropane through an aldol condensation reaction and a hydrogenation reaction.

Once the aldol condensation reaction is complete, dimethylolbutanal as an aldol reaction product, the unreacted raw material, and impurities having boiling points higher or lower than that of dimethylolbutanal coexist. Accordingly, it is important to efficiently separate a dimethylolbutanal from other aldol reaction products and feed the dimethylolbutanal component to a hydrogenation reaction.

Therefore, studies for separating dimethylolbutanal from other aldol reaction products by an economical method have been continuously conducted.

SUMMARY

The present specification relates to a method for producing dimethylolbutanal and a distillation device for producing same.

An exemplary embodiment of the present specification provides a method for producing dimethylolbutanal, the method comprising:

(A) distilling a raw material comprising dimethylolbutanal (DMB) in a distillation column;

(B) separating the distilled raw material in the distillation column into a low boiling point component, dimethylolbutanal, and a high boiling point component; and (C) refluxing a portion or all of the high boiling point component to the distillation column by heating the portion or all of the high boiling point component, in which the dimethylolbutanal is separated from a side cut of the distillation column.

Further, an exemplary embodiment of the present specification provides a distillation device comprising:

a distillation column provided so as to distill a raw material comprising dimethylolbutanal;

a raw material inlet provided such that the raw material is fed to the distillation column;

a second outlet provided such that a low boiling point component in which the raw material is distilled and separated is discharged from the distillation column;

a side cut provided such that dimethylolbutanal in which the raw material is distilled and separated is discharged from the distillation column; a first outlet provided such that a high boiling point component in which the raw material is distilled and separated is discharged from the distillation column; and a reboiler provided so as to reflux a portion or all of the high boiling point component discharged through the first outlet to the distillation column.

It is possible to obtain dimethylolbutanal used as a raw material for producing trimethylolpropane through a method for producing dimethylolbutanal according to an exemplary embodiment of the present specification with a high recovery rate.

Further, a distillation device according to an exemplary embodiment of the present specification may efficiently separate dimethylolbutanal in a short period of time by using a side cut of a distillation column.

BRIEF DESCRIPTION OF DRAWINGS

FIG. 1 is a schematic illustration of a distillation device for producing dimethylobutanal according to an exemplary embodiment of the present specification.

FIG. 2 is a schematic illustration of a distillation device according to the related art.

REFERENCE NUMERALS AND SYMBOLS USED HEREIN

11: Raw material inlet
12: Second outlet
13: Side cut
14: First outlet
15: Reflux pipe
100: Distillation column
200: Side cut equipment
300: Reboiler

DETAILED DESCRIPTION

Hereinafter, the present specification will be described in more detail.

In the present specification, the 'DMB recovery rate' is defined as a percentage of a value obtained by dividing an amount of dimethylolbutanal (DMB) comprised in a flow rate flowing out while being separated from the lower portion of a distillation column (distillation column) by an amount of DMB comprised in a raw material fed to the distillation column.

In the present specification, the 'side cut' means a middle part located at the side portion of the distillation column. That is, in the process of separating the raw material by distillation, the 'side cut' may mean a part in which a component separated from the middle portion of the distillation column is discharged. The side cut may mean a component except for components separated into the top portion of the tower and the bottom portion of the tower. In this case, a component separated into the side cut is referred to as a side draw stream.

In the present specification, a 'distillation column' may be used interchangeably with a 'distillation column'. That is, the distillation column and the distillation column are used as the same meaning.

An exemplary embodiment of the present specification provides a method for producing dimethylolbutanal, the method comprising: (A) distilling a raw material comprising dimethylolbutanal (DMB) in a distillation column; (B) separating the distilled raw material in the distillation column into a low boiling point component, dimethylolbutanal, and a high boiling point component; and (C) refluxing a portion or all of the high boiling point component to the distillation column by heating the portion or all of the high boiling point component, in which the dimethylolbutanal is separated from a side cut of the distillation column.

As dimethylolbutanal (DMB) and some byproducts, including salts, are produced in an aldol reaction, the reactivity and stability during the subsequent hydrogen reaction deteriorate when the salts are not removed. When trimethylolpropane (TMP) is produced by the hydrogenation reaction, it is necessary to effectively separate dimethylolbutanal (DMB) as a precursor material of trimethylolpropane after the first step aldol reaction.

In a related art method for separating an aldol reaction product, a distillation column and a wiped film evaporator (WFE) are used. The distillation column has a high separation efficiency, but effective components are lost because of the high-temperature operation of the reboiler and the long residence time during the separation process, and the distillation column needs to be operated at high vacuum to prevent the thermal decomposition of DMB. The wiped film evaporator has a small amount of thermally decomposed DMB due to characteristics of the device in which the aldol reaction product is separated within a short time, but has a disadvantage in that the separation efficiency is reduced. Thus, to increase the separation efficiency, the WFE needs to be repeatedly operated, or by increasing the number of devices, which is not desirable.

Accordingly, the present inventors have invented a device and a process for efficiently separating effective components (DMB, and the like) in a short period of time by using a side cut function at the side portion of the distillation column having a high separation efficiency. Through this method, the side reaction and the thermal decomposition of DMB can be reduced by minimizing the exposure of the aldol reaction product to high temperature in the reboiler, the amount of energy used can be reduced by decreasing the amount of DMB residing in the reboiler, and the content of the high boiling point component in the raw material finally fed to the hydrogenation process can be reduced, so that the hydrogenation reactivity is increased, and the catalyst is protected.

According to an exemplary embodiment of the present specification, step (A) may further comprise: obtaining an aldol reaction product by allowing an alkanal, formaldehyde (FA) and an alkylamine catalyst to react; and obtaining a raw material comprising the dimethylolbutanal by extracting the aldol reaction product together with an alcohol solvent.

In other words, the raw material in step (A) may be a raw material obtained by a step of extracting a product obtained by allowing an alkanal, formaldehyde (FA), and an alkylamine catalyst to react using an alcohol solvent.

As for a condition under which the aldol reaction raw material is fed, based on 1 mol of an alkanal, the higher the amount of formaldehyde included as one of the reaction raw materials in the feed, the better the reaction yield. However, considering that the theoretical equivalent ratio required for the reaction, the alkanal:formaldehyde=1:2, an excess of formaldehyde is included in the feed, that is, the formaldehyde in an amount of 2 mol or more remains after the reaction, which may be undesirable in terms of process configuration and economic feasibility because formaldehyde needs to be reused through the separation/recovery process after the reaction. Accordingly, a suitable amount of formaldehyde included in the feed may be selected in consideration of the possible increase of reaction yield and the proportion of formaldehyde included in excess in the feed.

According to an exemplary embodiment of the present specification, a mol ratio of the alkanal, the formaldehyde, and the alkylamine catalyst may be 2.5 mol to 5 mol of formaldehyde and 0.1 mol to 0.3 mol of the alkylamine catalyst based on 1 mol of the alkanal. That is, the mol ratio of the alkanal:formaldehyde:an alkylamine catalyst may be 1:2.5 to 5:0.1 to 0.3. Further, a mol ratio of the alkanal, the formaldehyde, and the alkylamine catalyst may be 3.5 mol to 4.5 mol of formaldehyde and 0.15 mol to 0.25 mol of the alkylamine catalyst based on 1 mol of the alkanal.

When the content of formaldehyde is less than 2.5 mol based on 1 mol of the alkanal, the reaction yield may rapidly decrease, and when the content is more than 5 mol, the amount of formaldehyde recovered after the reaction may rapidly increase compared to the increase in the reaction yield, so that the economic feasibility may deteriorate. Further, when the content of the alkylamine catalyst is less than 0.1 mol based on 1 mol of the alkanal, the reaction rate slows down and the reaction time is increased, and when the content is more than 0.3 mol, the economic feasibility may deteriorate because the catalyst is used in a large amount.

According to an exemplary embodiment of the present specification, the aldol reaction of the alkanal, the formaldehyde (FA), and the alkylamine catalyst may be performed at a temperature of 25° C. to 50° C. at normal pressure. Preferably, the temperature may be 30° C. to 40° C. Further, according to an exemplary embodiment of the present specification, the aldol reaction time may be 90 minutes to 200 minutes, preferably 120 minutes to 200 minutes. According to an exemplary embodiment of the present specification, when the temperature and time conditions of the aldol reaction are satisfied, the reaction yield may be increased.

According to an exemplary embodiment of the present specification, the alkanal may be an alkanal having 3 to 10 carbon atoms, and specifically, may be propanal, butanal, pentanal, hexanal, and the like, but is not limited thereto. More specifically, n-butanal (n-BAL) is preferred.

According to an exemplary embodiment of the present specification, the alkylamine in the alkylamine catalyst is an alkylamine having 3 to 20 carbon atoms, and specifically, trimethylamine, triethylamine (TEA), tripropylamine, diisopropylethylamine, or the like may be used, and preferably, triethylamine may be used.

According to an exemplary embodiment of the present specification, the alcohol solvent used as an extraction solvent in the extraction of the product may be an alcohol solvent having 2 to 10 carbon atoms. Specifically, the alcohol solvent may be an alcohol solvent having 6 to 8 carbon atoms, and may be preferably an alcohol solvent having 8 carbon atoms.

According to an exemplary embodiment of the present specification, the alcohol solvent may be 2-ethyl hexanol (2-EH).

According to an exemplary embodiment of the present specification, the extraction solvent may be fed in an amount 1.5 times to 3 times greater than the initial raw material weight of the aldol reaction.

According to an exemplary embodiment of the present specification, the extraction temperature during the extraction of the product is preferably 25° C. to 90° C., and specifically, the extraction temperature is preferably 30° C. to 70° C. According to an exemplary embodiment of the present specification, when the extraction temperature is satisfied, the extraction yield may be increased.

According to an exemplary embodiment of the present specification, the distillation column may be a single distillation column or a multi-stage distillation column, and is not limited thereto, but may be preferably a multi-stage distillation column.

According to an exemplary embodiment of the present specification, the distillation column may be a multi-stage distillation column of 20 stages to 40 stages. The distillation column may be preferably a multi-stage distillation column of 20 stages to 30 stages, and more preferably a tray type multi-stage distillation column of 25 stages. When the number of stages of the distillation column is less than 20, the DMB recovery rate may be reduced, and when the number of stages of the distillation column is more than 40, the DMB recovery rate may be increased, but as the number of stages of the distillation column is increased, device investment costs and operation costs may be increased.

According to an exemplary embodiment of the present specification, the low boiling point component in step (B) may be separated into the top portion of the distillation column. The low boiling point component may mean a material having a lower boiling point than that of DMB. Examples thereof comprise formaldehyde (FA), water ($H_2O$), methanol (MeOH), triethylamine (TEA), ethylacrolein (EA), and the like. The fact that the low boiling point component is separated into the top portion of the distillation column may mean that the low boiling point component is present in the highest amount of all components separated into the top portion of the distillation column as compared to the content of the low boiling point component separated into the bottom portion and the side cut of the distillation column. Alternatively, the fact that the low boiling point component is separated into the top portion of the distillation column may mean that the low boiling point component is not present in the component separated into the bottom portion and the side cut of the distillation column.

According to an exemplary embodiment of the present specification, the high boiling point component in step (B) may be separated into the bottom portion of the distillation column. The high boiling point component may mean a material having a higher boiling point than that of DMB. Examples thereof comprise trimethylolpropane (TMP), and the like. The fact that the high boiling point component is separated into the bottom portion of the distillation column may mean that the high boiling point component is present in the highest amount of all the components separated into the bottom portion of the distillation column as compared to the content of the high boiling point component separated into the top portion of and the side cut of the distillation column. Alternatively, the fact that the high boiling point component is separated into the bottom portion of the distillation column may mean that the high boiling point component is not present in the component separated into the top portion and the side cut of the distillation column.

According to an exemplary embodiment of the present specification, the top portion of the distillation column may mean a portion located at the highest point in the upper portion of the distillation column. The top portion of the distillation column may mean a stage located at the uppermost portion of a tray type multi-stage distillation column. The bottom portion of the distillation column may mean a portion located at the lowest point in the lower portion of the distillation column. The bottom portion of the distillation column may mean a stage located at the lowermost portion of a tray type multi-stage distillation column.

According to an exemplary embodiment of the present specification, the dimethylolbutanal may be separated at a recovery rate of 94% or more, more preferably 98% or more. In this case, the dimethylolbutanal may be separated from the side cut located at the side portion of the distillation column. The fact that the dimethylolbutanal is separated into the side cut of the tower in the distillation column may mean that the dimethylolbutanal is comprised in the highest content in the component separated into the side cut as compared to the content of the dimethylolbutanal comprised in the component separated into the top portion of the tower and the bottom portion of the tower in the distillation column. Alternatively, the fact that the dimethylolbutanal is separated into the side cut of the tower in the distillation column may mean that the dimethylolbutanal is not separated into the top portion and the bottom portion of the distillation column.

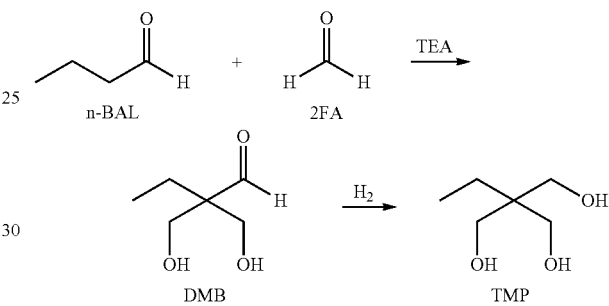

In order to produce a TMP product through a hydrogenation processing method, a two-step process including an aldol reaction and a hydrogenation reaction is performed, as shown in the chemical reaction above. Since the DMB produced by the aldol reaction is an intermediate material in an unstable state in which aldehyde is present due to the structure thereof, the DMB is characterized in that the DMB may thermally decompose easily or may cause a side reaction according to the synthesis conditions or separation conditions.

In contrast, since TMP is a final product comprising a stable alcohol structure in which the hydrogenation reaction is also complete, TMP is characterized in that in the separation process, a thermal decomposition or a side reaction does not occur easily, and accordingly, TMP can be separated by using a general distillation column.

Accordingly, it is very important to separate a target material when an unstable intermediate such as DMB is separated, and to minimize the thermal decomposition thereof or minimize the side reaction in the separation process, but when a stable product such as TMP is separated, it is a very important to use a small amount of energy while efficiently separating the target material.

Due to this background, it can be seen that a method for separating DMB from the reaction product and a method of separating TMP from the reaction product are fundamentally different in terms of separation methods, conditions, devices, and the like.

Further, when a stable product such as TMP is separated, TMP is stable even though TMP resides in the column for a long period of time, so that two column functions may be integrated in one column instead of using two columns by applying a divided wall column (DWC), and the like, and accordingly, it is possible to expect lower energy and investment costs. However, when an unstable product such as DMB is separated, the residence time in the column is increased when a DWC is used, and the use of DWC is not preferred because it is likely that DMB will be thermally decomposed. That is, when an unstable material is separated, it is very important to separate a target material in a short time by minimizing the residence time in the column while minimizing the exposure of the unstable material to high temperature.

Accordingly, a method of separating DMB from the reaction product and a method of separating TMP from the reaction product are fundamentally different in terms of separation methods, conditions, devices, and the like.

According to an exemplary embodiment of the present specification, the pressure at the top portion of the distillation column may be 150 mbar to 650 mbar, and 200 mbar to 600 mbar. The pressure may be selected in connection with a suitable range of the operation temperature of the column. When the pressure at the top portion of the distillation column is less than 150 mbar, components having low boiling points separated from the top of the tower at high vacuum are condensed and recovered, which may be undesirable during operation of the distillation column because the cooling temperature of the top portion of the distillation column is lowered, and when the pressure is more than 650 mbar, an effective component may be decomposed because the column temperature needs to be 200° C. or more to separate the effective component.

According to an exemplary embodiment of the present specification, the heating temperature in step (C) may be 150° C. to 200° C. In this case, the heating temperature may mean a set temperature of a reboiler. In addition, the heating temperature in step (C) may be 160° C. to 195° C. The minimum heating temperature for separating an effective component (DMB) is required, and when the heating temperature in step (C) is less than 150° C., it may be difficult to separate low boiling point components into the upper portion of the distillation column at a suitable flow rate, and when the heating temperature in the step (C) is more than 200° C., the effective component (DMB) may be decomposed at high temperature, which is not preferred.

Furthermore, an exemplary embodiment of the present specification provides a distillation device comprising: a distillation column to distill a raw material comprising dimethylolbutanal; a raw material inlet provided such that the raw material is fed to the distillation column; a second outlet provided such that a low boiling point component in which the raw material is distilled and separated is discharged from the distillation column; a side cut provided such that dimethylolbutanal in which the raw material is distilled and separated is discharged from the distillation column; a first outlet provided such that a high boiling point component in which the raw material is distilled and separated is discharged from the distillation column; and a reboiler provided so as to reflux a portion or all of the high boiling point component discharged through the first outlet to the distillation column.

In the method of separating DMB by using a distillation column, when a side cut is used, a side reaction and the thermal decomposition of DMB may be decreased by minimizing the exposure of an aldol reaction product to high temperature in a reboiler, and the amount of energy used may be reduced and DMB may be separated at a high recovery rate by decreasing the amount of DMB residing in the reboiler. This may ultimately reduce the content of the high boiling point component in a raw material fed to the hydrogenation process, so that there are effects capable of improving the hydrogenation reactivity and protecting a catalyst.

According to an exemplary embodiment of the present specification, the distillation column may be a single distillation column or a multi-stage distillation column, and is not limited thereto, but may be preferably a multi-stage distillation column having 20 stages to 40 stages. When the number of stages of the distillation column is less than 20, the DMB recovery rate may be reduced, and when the number of stages of the distillation column is more than 40, the DMB recovery rate may be increased, but as the number of stages of the distillation column is increased, device investment costs and operation costs may be increased.

According to an exemplary embodiment of the present specification, the raw material inlet may be located at the side portion of the distillation column. When the distillation column according to an exemplary embodiment of the present specification is a multi-stage distillation column with 20 stages to 40 stages, the raw material inlet may be located between the 5th stage and the 35th stage of the distillation column. Preferably, the raw material inlet may be located between the 5th stage and the 20th stage of the distillation column. More preferably, the raw material inlet may be located between the 10th stage and the 15th stage of the distillation column.

According to an exemplary embodiment of the present specification, the first outlet may be located at the bottom portion of the tower in the distillation column. The bottom portion of the tower in the distillation column may mean a portion located at the lowest point in the lower portion of the distillation column. The bottom portion of the tower in the distillation column may mean a stage located at the lowermost portion of a tray type multi-stage distillation column. The component separated into the first outlet may comprise a high boiling point component. The description of the high boiling point component is the same as that described above.

According to an exemplary embodiment of the present specification, the second outlet may be located at the top portion of the distillation column. The top portion of the distillation column may mean a portion located at the highest point in the upper portion of the distillation column. The top portion of the distillation column may mean a stage located at the uppermost portion of a tray type multi-stage distillation column. The component separated into the second outlet may comprise a low boiling point component. The description of the low boiling point component is the same as that described above.

According to an exemplary embodiment of the present specification, the side cut may be located at the side portion of the distillation column. The side cut may be located between the raw material inlet and the first outlet. Specifically, the side cut may be located between the 2nd stage and the 10th stage of the distillation column. Preferably, the side cut may be located between the 2nd stage and the 5th stage of the distillation column.

According to an exemplary embodiment of the present specification, the gap between the side cut and the raw material inlet may be the 3rd stage to the 30th stage. Preferably, the gap between the side cut and the raw material inlet may be the 5th stage to the 10th stage. In this case, the raw material inlet may be located at a higher stage than the side cut.

According to an exemplary embodiment of the present specification, the reboiler is connected to a portion of a bottom line connected to the bottom portion of the distillation column, and thus may serve to reflux a component comprising a high boiling point material separated into the bottom portion of the distillation column to the lower portion of the distillation column. The bottom line may mean a pipe which is connected to the bottom portion of the distillation column and through which a component comprising a high boiling point material is separated and discharged.

According to an exemplary embodiment of the present specification, the temperature of the reboiler may be adjusted to 150° C. to 200° C. Preferably, the temperature of the reboiler may be adjusted to 160° C. to 195° C.

According to an exemplary embodiment of the present specification, the reboiler may further comprise a temperature adjusting means provided to adjust the temperature of the reboiler to 150° C. to 200° C. Preferably, the temperature adjusting means may be provided to adjust the temperature to 160° C. to 195° C.

The temperature adjusting means may mean a temperature display window, a heating means, a temperature controlling means, and the like, and is not limited as long as the temperature adjusting means is typically used in the reboiler in the related art.

FIG. 1 is a schematic view of the distillation device and pipe configuration for performing the method for producing dimethylolbutanal according to an exemplary embodiment of the present specification.

As illustrated in FIG. 1, a raw material comprising dimethylolbutanal (DMB) is fed to a distillation column 100 through a raw material inlet 11. The raw material comprising dimethylolbutanal (DMB) is obtained by extracting an aldol reaction product obtained by subjecting an alkanal, formaldehyde, and an alkylamine catalyst to an aldol condensation reaction using an alcohol solvent. In this case, the alkanal may be an alkanal having 3 to 10 carbon atoms, and specifically, may be propanal, butanal, pentanal, hexanal, and the like, but is not limited thereto. More specifically, n-butanal (n-BAL) is preferred. In addition, the alkylamine catalyst is an alkylamine having 3 to 20 carbon atoms, and specifically, trimethylamine, triethylamine (TEA), tripropylamine, diisopropylethylamine, or the like may be used, and preferably, triethylamine may be used. The alcohol solvent used as an extraction solvent in the extraction of the aldol reaction product may be an alcohol solvent having 2 to 10 carbon atoms. Specifically, the alcohol solvent may be an alcohol solvent having 6 to 8 carbon atoms, and may be preferably an alcohol solvent having 8 carbon atoms. Specifically, it is preferred that the alcohol solvent is 2-ethyl hexanol (2-EH). In this case, 2-ethyl hexanol may be fed by 1.5 times to 3 times as compared to the initial raw material weight of the aldol condensation reaction, and the extraction temperature may be 25° C. to 90° C.

The distillation column 100 may be a single distillation column or a multi-stage distillation column, and is not limited thereto, but may be preferably a multi-stage distillation column. In this case, the distillation column 100 may be a multi-stage distillation column having 20 stages to 40 stages. Furthermore, the pressure at the top portion of the distillation column 100 may be 150 mbar to 650 mbar.

As illustrated in FIG. 1, the raw material inlet 11 may be located at the side portion of the distillation column 100. When the distillation column 100 is a multi-stage distillation column having 20 stages to 40 stages, the raw material inlet 11 may be located between the 5th stage and the 35th stage of the distillation column 100.

The first outlet 14 may be located at the bottom portion of the distillation column 100. The bottom portion of the distillation column 100 may mean a portion located at the lowest point in the lower portion of the distillation column 100. The bottom portion of the distillation column 100 may mean a stage located at the lowermost portion of a tray type multi-stage distillation column. The component separated into the first outlet 14 may comprise a high boiling point componen. The high boiling point component may mean a material having a higher boiling point than that of DMB. Examples thereof comprise trimethylolpropane (TMP), and the like. The fact that the high boiling point component is separated into the first outlet 14 of the distillation column 100 may mean that the high boiling point component is present in the highest amount among the components separated into the first outlet 14 as compared to the content of the high boiling point component separated into the second outlet 12 and the side cut 13 of the distillation column 100.

The second outlet 12 may be located at the top portion of the distillation column 100. The top portion of the distillation column 100 may mean a portion located at the highest point in the upper portion of the distillation column 100. The top portion of the distillation column 100 may mean a stage located at the uppermost portion of a tray type multi-stage distillation column. The component separated into the second outlet 12 may comprise a low boiling point component. The low boiling point component may mean a material having a lower boiling point than that of DMB. Examples thereof comprise formaldehyde (FA), water ($H_2O$), methanol (MeOH), triethylamine (TEA), ethylacrolein (EA), and the like. The fact that the low boiling point component is separated into the second outlet 12 of the distillation column 100 may mean that the low boiling point component is present in the highest amount among the components separated into the second outlet 12 as compared to the amount of the low boiling point component separated into the first outlet 14 and the side cut 13 of the distillation column 100.

The side cut 13 may be located at the side portion of the distillation column 100. The side cut 13 may be connected to a portion in which side cut equipment 200 of the distillation column 100 is located. The side cut equipment 200 is a device capable of capturing a liquid flowing down from the raw material inlet 11 of the distillation column 100. A portion of the captured liquid is separated into the side cut 13, and the remaining portion flows down to the lower portion of the distillation column 100 and is separated into the first outlet 14.

The side cut 13 may be located between the raw material inlet 11 and the first outlet 14. Specifically, the side cut equipment 200 may located between the 2nd stage and the 10th stage of the distillation column 100. The gap between the side cut 13 and the raw material inlet 11 may be the 3rd stage to the 30th stage. In this case, the raw material inlet 11 may be located at a higher stage than the side cut 13.

The fact that the dimethylolbutanal is separated into the side cut 13 of the distillation column 100 may mean that the dimethylolbutanal is present in the highest amount of all the components separated into the side cut 13 as compared to the content of the dimethylolbutanal separated into the second outlet 12 and the first outlet 14 of the distillation column 100.

The reboiler 300 is connected to a portion of the first outlet 14 connected to the bottom portion of the distillation column 100, and thus may serve to reflux a component comprising a high boiling point material separated into the first outlet 14 again to the lower portion of the distillation column 100 through a reflux pipe 15. The temperature of the reboiler 300 may be adjusted to 150° C. to 200° C.

As described above, according to an exemplary embodiment of the present specification, DMB may be efficiently separated from the aldol reaction product by using side cut equipment in a distillation column having a high separation efficiency.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

<Preparation Example 1> Preparation of Distillation Raw Material n-butanal (n-BAL), formaldehyde (FA), and triethylamine (TEA) were prepared at a mol ratio of 1:4:0.2, and allowed to react under a condition of 35° C. at normal pressure for 3 hours. Subsequently, 2-ethyl hexanol (2-EH) was fed 2 times as compared to the initial raw material weight, and an organic layer obtained by extracting the product under a condition of 70° C. at normal pressure was prepared as a distillation raw material.

A representative composition of the obtained distillation raw material is shown in the following Table 1.

<Preparation Example 2> Preparation of Distillation Raw Material n-butanal (n-BAL), formaldehyde (FA), and triethylamine (TEA) were prepared at a mol ratio of 1:2:0.2, and allowed to react under a condition of 35° C. at normal pressure for 3 hours. Subsequently, 2-ethyl hexanol (2-EH) was fed 2 times as compared to the initial raw material weight, and an organic layer obtained by extracting the product under a condition of 70° C. at normal pressure was prepared as a distillation raw material.

A representative composition of the obtained distillation raw material is shown in the following Table 1.

TABLE 1

| | Classification (wt %) | | | | |
|---|---|---|---|---|---|
| | $H_2O$ | Low boiling point component | 2-EH | DMB | High boiling point component |
| Preparation Example 1 | 4.6 | 6.9 | 78.3 | 7.8 | 2.4 |
| Preparation Example 2 | 4.3 | 10.0 | 78.2 | 4.5 | 3.0 |

Example 1

By using a 25-stage tray type distillation column having a diameter of 50 mm, a raw material feed stage and a side cut stage were installed at the 13th stage and the 3rd stage, respectively. The pressure at the upper portion of the distillation column was set at 200 mbar, and the temperature of the reboiler was adjusted to 160° C.

While the raw material obtained in Preparation Example 1 was supplied constantly at a rate of 10 g/min, a continuous operation was performed for 3 hours until the column condition was stabilized.

Under a condition in which the column condition was stabilized, the flow rate and the composition of an organic material at the side cut stage, and the DMB recovery rate are summarized in the following Table 2.

Example 2

A continuous operation was performed in the same manner as in Example 1, except that the pressure at the upper portion of the distillation column was set at 600 mbar, and the reboiler was operated by adjusting the temperature of the reboiler to 195° C. in Example 1.

Under a condition in which the column condition was stabilized, the flow rate and the composition of an organic material at the side cut stage, and the DMB recovery rate are summarized in the following Table 2.

Example 3

A continuous operation was performed in the same manner as in Example 1, except that the pressure at the upper portion of the distillation column was set at 200 mbar, the reboiler was operated by adjusting the temperature of the reboiler to 200° C., and the raw material obtained in Preparation Example 2 was supplied constantly at a rate of 11.5 g/min in Example 1.

Under a condition in which the column condition was stabilized, the flow rate and the composition of an organic material at the side cut stage, and the DMB recovery rate are summarized in the following Table 2.

Comparative Example 1

An experiment was performed in a state where the side cut equipment was removed from the distillation column device used in Example 1. The pressure at the upper portion of the distillation column was set at 800 mbar, and while the reboiler was operated by adjusting the temperature of the reboiler to 190° C., a continuous operation was performed for 3 hours until the column condition was stabilized.

Under a condition in which the column condition was stabilized, the flow rate and the composition of an organic material discharged from the reboiler, and the DMB recovery rate are summarized in the following Table 2.

Comparative Example 2

A continuous operation was performed in the same manner as in Comparative Example 1, except that the pressure at the upper portion of the distillation column was set at 200 mbar, and the reboiler was operated by adjusting the temperature of the reboiler to 150° C. in Comparative Example 1.

Under a condition in which the column condition was stabilized, the flow rate and the composition of an organic material discharged from the reboiler, and the DMB recovery rate are summarized in the following Table 2.

Comparative Example 3

A DMB separation experiment was performed by using a wiped film evaporator (WFE) device. The experiment was performed under the conditions of a pressure of 200 mbar and a temperature of 150° C., and the raw materials obtained in the Preparation Examples were supplied constantly at 10 g/min to the device.

In this case, a rotor provided inside the evaporator was operated at a rate of 150 rpm, the low boiling point component was removed into the upper portion of the WFE, and the DMB component was continuously separated into the lower portion of the WFE.

The flow rate and the composition of an organic material separated into the lower portion of the device, and the DMB recovery rate are summarized in the following Table 2.

TABLE 2

| Classification | | | | | Low | | | High | |
|---|---|---|---|---|---|---|---|---|---|
| | Separation method and position | Operation condition Pressure/ Temperature | Flow rate (g/min) | H$_2$O (wt %) | boiling point component (wt %) | 2-EH (wt %) | DMB (wt %) | boiling point component (wt %) | DMB recovery rate (%) |
| Example 1 | column side cut | 200 mbar/ 160° C. | 8.1 | 2.0 | 0.5 | 87.0 | 9.5 | 1.0 | 98.7 |
| Example 2 | column side cut | 600 mbar/ 195° C. | 8.2 | 1.4 | 0.4 | 88.0 | 9.4 | 0.8 | 98.8 |
| Example 3 | column side cut | 200 mbar/ 200° C. | 9.4 | 1.4 | 2.9 | 88.0 | 5.2 | 2.5 | 94.5 |
| Comparative Example 1 | column bottom | 800 mbar/ 190° C. | 8.5 | 1.7 | 1.2 | 82.0 | 8.0 | 7.1 | 87.2 |
| Comparative Example 2 | column bottom | 200 mbar/ 150° C. | 8.2 | 1.2 | 1.0 | 83.2 | 8.7 | 5.9 | 91.5 |
| Comparative Example 3 | WFE bottom | 200 mbar/ 150° C. | 7.5 | 2.0 | 6.0 | 81.5 | 8.0 | 2.5 | 76.9 |

According to Table 2, it could be confirmed that according to an exemplary embodiment of the present specification, in the case of Examples 1 and 2 in which DMB was separated from a distillation column which was equipped with a side cut, a higher DMB recovery rate (98.7% or more) could be obtained as compared to Comparative Examples 1 and 2 in which the distillation column in the related art, which was not equipped with a side cut, was used, and Comparative Example 3 in which a wiped film evaporator was used.

As a result, when the distillation device according to an exemplary embodiment of the present specification was used, a side reaction and the thermal decomposition of DMB was decreased by minimizing the exposure of an aldol reaction product to high temperature in a reboiler, and the amount of energy used was reduced by decreasing the amount of DMB residing in the reboiler, so that the DMB component could be efficiently separated in a short period of time.

As a result, the hydrogenation reactivity may be improved and the catalyst may be protected by decreasing the content of the high boiling point component in the raw material fed to the hydrogenation process.

Furthermore, when Examples 1, 2, and 3 are compared, it can be seen that when a mol ratio of the alkanal:formaldehyde:the alkylamine catalyst satisfies 1:2.5 to 5:0.1 to 0.3, a higher DMB recovery rate may be obtained.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for producing dimethylolbutanal, the method comprising:
   (A) distilling a raw material comprising dimethylolbutanal (DMB) in a distillation column to prepare a distilled raw material;
   (B) separating the distilled raw material in the distillation column into a low boiling point component, dimethylolbutanal, and a high boiling point component; and
   (C) refluxing a portion or all of the high boiling point component in the distillation column by heating the portion or all of the high boiling point component,
   wherein the dimethylolbutanal is separated from a side cut of the distillation column.

2. The method of claim 1, wherein step (A) further comprises:
   obtaining an aldol reaction product by reacting an alkanal, formaldehyde (FA), and an alkylamine catalyst; and
   obtaining a raw material comprising the dimethylolbutanal by extracting the aldol reaction product with an alcohol solvent.

3. The method of claim 2, wherein a mol ratio of the alkanal, the formaldehyde, and the alkylamine catalyst is 2.5 mol to 5 mol of formaldehyde and 0.1 mol to 0.3 mol of the alkylamine catalyst based on 1 mol of the alkanal.

4. The method of claim 1, wherein the distillation column is a multi-stage distillation column comprising 20 stages to 40 stages.

5. The method of claim 1, wherein the low boiling point component in step (B) is separated into a top portion of the distillation column.

6. The method of claim 1, wherein the high boiling point component in step (B) is separated into a bottom portion of the distillation column.

7. The method of claim 1, wherein the dimethylolbutanal is separated at a recovery rate of 94% or more.

8. The method of claim 1, wherein the heating temperature in step (C) is 150° C. to 200° C.

9. The method of claim 1, wherein a pressure at a top portion of distillation column is 150 mbar to 650 mbar.

10. A distillation device comprising:
    a distillation column for distilling a raw material comprising dimethylolbutanal;
    a raw material inlet for feeding the raw material to the distillation column;
    a second outlet for discharging a low boiling point component from the distillation column;
    a side cut for discharging dimethylolbutanal from the distillation column;
    a first outlet for discharging a high boiling point component from the distillation column; and
    a reboiler for refluxing a portion or all of the high boiling point component discharged through the first outlet to the distillation column.

11. The distillation device of claim 10, wherein the distillation column is a multi-stage distillation column having 20 stages to 40 stages.

12. The distillation device of claim 11, wherein the raw material inlet is located between a 5th stage and a 35th stage of the distillation column.

13. The distillation device of claim 10, wherein the first outlet is located at a bottom portion of the distillation column.

14. The distillation device of claim 10, wherein the side cut is located between the raw material inlet and the first outlet.

15. The distillation device of claim 11, wherein the side cut is located between a 2nd stage and a 10th stage of the distillation column.

16. The distillation device of claim 10, wherein the second outlet is located at a top portion of the distillation column.

17. The distillation device of claim 10, further comprising a temperature adjusting means to adjust a temperature of the reboiler to 150° C. to 200° C.

* * * * *